United States Patent [19]

Berwing et al.

[11] Patent Number: 4,832,941

[45] Date of Patent: May 23, 1989

[54] CONTRAST MEDIUM FOR ULTRASONIC EXAMINATIONS AND PROCESS FOR ITS PREPARATION

[75] Inventors: Klaus Berwing; Martin Schlepper, both of Bad Nauheim, Fed. Rep. of Germany

[73] Assignee: Max-Planck-Gesellschaft zur Forderung der Wissenschaften e.V, Fed. Rep. of Germany

[21] Appl. No.: 896,334

[22] Filed: Aug. 14, 1986

[30] Foreign Application Priority Data

Aug. 14, 1985 [DE] Fed. Rep. of Germany ....... 3529195

[51] Int. Cl.⁴ .................. A61K 9/40; A61K 19/22; A61K 19/52; A61K 31/155; A61K 33/26
[52] U.S. Cl. ........................... 424/9; 424/47; 514/184
[58] Field of Search ............ 424/9, 19, 147, 37; 367/87; 514/184

[56] References Cited

FOREIGN PATENT DOCUMENTS 3324745 11/1984 Fed. Rep. of Germany .

OTHER PUBLICATIONS

Armstrong, William F., Mueller, Thomas M., Kinney, Evlin L., Tickner, E. Glenn, Dillon, James C. and Feisenbaum, Harvey, Assessment of Mycardinol Perfasim Abnormalitise With Contrast-Enhanced Two-Dimensional Echocardiography, Circulation 66:(1) pp. 166-173 (1982).

*Primary Examiner*—Stanley J. Friedman
*Attorney, Agent, or Firm*—Lowe, Price, LeBlanc, Becker & Shur

[57] ABSTRACT

A contrast medium for ultrasonic examinations, in particular for echocardiography, based on a suspension of gas bubbles in a pharmacologically acceptable, aqueous liquid vehicle having a physiological electrolyte content, containing (A) a pharmacologically acceptable polypeptide and/or polysaccharide and/or a derivative thereof,
(B) a pharmacologically acceptable vegetable oil and
(C) a pharmacologically acceptable soluble iron(III) salt, and a process for its preparation. This contrast medium is able to penetrate the pulmonary capillaries and thus makes possible, after intravenous injection, inter alia echocardiographic examination of the left ventricle.

10 Claims, No Drawings

CONTRAST MEDIUM FOR ULTRASONIC EXAMINATIONS AND PROCESS FOR ITS PREPARATION

The invention relates to a contrast medium for ultrasonic examinations, in particular for echocardiography based on a suspension of gas bubbles in a pharmacologically acceptable aqueous liquid vehicle having a physiological electrolyte content.

The examination of internal organs of humans and animals with ultrasound is a diagnostic method which was introduced some time ago and has been practised since then and which is based on the reflection of ultrasonic waves in the megahertz range (above 2 MHz) at the interfaces between different types of tissue. The echoes produced by this are amplified and displayed. Particularly important in this connection is contrast medium echocardiography which is used for the diagnosis of cardiopathies both in the M-mode and in two-dimensional echocardiography. This entails intravenous injection of a contrast medium to produce an ultrasonic echo in those regions where the contrast medium is located, which makes it possible to diagnose right cardiopathies including atrial and ventricular septum defects, the problem with diagnosis of left cardiopathies by this method being that it is necessary to deliver the contrast medium via a catheter introduced into the left ventricle or in the pulmonary capillary region (R.S. Meltzer et al., Brit. Heart J. 44 (1980), 390; R.S. Meltzer et al., Med. & Biol. 6 (1980), 263; C. Mortera et al., Eur. J. Cardiol. 9/6 (1979), 437; A. Reale et al., Eur. Heart J. 1 (1980), 101 and J. Roelandt et al., Echocardiology, Martinus Nijhoff, Den Haag, Boston, London (1981) 219).

Various contrast media for ultrasonic echocardiography have already been described, such as hydrogen peroxide (W.F. Armstrong et al., Circulation 66: Suppl. II (1982), II-256), sodium chloride solution enriched with carbon dioxide (A.N. De Maria et al., Circulation 60: Suppl. II (1980), II-143), a mixture of Renografin® and sodium chloride (G. Maurer et al., J. Am. Coll. Cardiol. I(II) (1983), 645), gelatin-encapsulated microscopic bubbles (W.F. Armstrong et al., Circulation 66 (1982), 166), gas bubbles stabilized in various ways (J. Folkert et al., JACC, Vol. 3, No. 5 (1984), 1219–1226) and gas bubbles stabilized by microparticles (German Offenlegungsschrift No. 3,324,745 and European Published Specification No. 0,052,575).

Even though these customary contrast media produce gas bubbles with a particle size of about 10 μm or slightly less (see European Published Specification No. 0,052,575 and J. Folkert et al., loc. cit.), these customary contrast media are unsatisfactory specifically with regard to the particle size and the stability of the gas bubbles, so that it has not hitherto become possible to use contrast media of this type for echocardiographic visualization of the left ventricle by injection of contrast medium into a peripheral vein.

Hence the object of the present invention is to produce a contrast medium which is suitable for ultrasonic examinations and, in particular, for echocardiography, which is non-toxic, contains microscopic bubbles of air or other gases in adequate concentration and stability, specifically with a particle size below 8 μm, so that these microscopic bubbles are able to pass through the pulmonary capillaries, which will make possible the diagnosis of left cardiopathies by ultrasonic examination without using a cathether.

This object has now been achieved by the characterizing features of the contrast medium according to the main claim. The subclaims relate to particularly preferred embodiments of the subject-matter of this invention, and to a process for the preparation of the claimed contrast medium.

Thus the invention relates to a contrast medium for ultrasonic examinations and, in particular, for echocardiography, based on a suspension of gas bubbles in a pharmacologically acceptable aqueous liquid vehicle having a physiological electrolyte content, which is characterized in that the liquid vehicle contains (A) a pharmacologically acceptable, that is to say nontoxic and non-antigenic, polypeptide and/or polysaccharide and/or a derivative thereof, (B) a pharmacologically acceptable vegetable oil and (C) a pharmacologically acceptable soluble iron(III) salt.

This contrast medium makes it possible to entrap air in the form of microscopic bubbles, 100% of which are smaller than 6.4 μm on manual suspension of the air, and 100% of which are smaller than 3.9 μm in an agitated system. At the same time, the contrast medium is distinguished by its osmolality being low and its being well tolerated. This contrast medium makes it possible for the first time, owing to this smallness of the microscopic bubbles and its being well tolerated, for the microscopic bubbles to be able to pass through the pulmonary capillaries in a sufficient amount, and thus to be detectable in the left atrium, in the left ventricle and in the ascending aorta. This has been demonstrated in 27 patients, and this will be dealt with in detail hereinafter. Since the microscopic bubbles are suspended in blood, it is possible to visualize the blood flow so that it is possible directly and non-invasively to detect pathological states in the right and in the left half of the heart. Hence it become possible with the aid of the contrast medium according to the invention, in virtually non-invasive ways, merely by peripheral intravenous injection, to draw conclusions about the flow properties in the left segments of the heart, about regurgitation at the mitral and aortic valves, about left-right shunts, about arterial ultrasonography and, moreover, about myocardial perfusion.

Owing to the smallness of the gas bubbles contained in the contrast medium according to the invention there is no risk of embolism whatever, since the red blood corpuscles are larger on average than are the gas bubbles, namely 6 μm in diameter.

The contrast medium according to the invention contains as constituent A, namely as pharmacologically acceptable polypeptide and/or polysaccharide or derivative thereof, preferably gelatin, gelatin derivatives, such as oxypolygelatin, degraded gelatin, gelatin polysuccinate, crosslinked polypeptides, dextrans, crosslinked dextrans or mixtures thereof.

The second constituent which the contrast medium according to the invention contains is a pharmacologically acceptable vegetable oil which has the purpose of stabilizing the air bubbles in the aqueous liquid vehicle which contains constituent A. The pharmacologically acceptable vegetable oil which can be used according to the invention is preferably soya oil, maize oil, sesame oil, arachis oil or mixtures thereof. Fractionated soya oil of medicinal quality is used with particular advantage.

The contrast medium according to the invention contains as constituent C a pharmacologically acceptable soluble iron(III) salt which likewise has the purpose of stabilizing the gas bubbles and of reducing the surface tension of the contrast medium. It is possible to use any desired solutions containing triply charged iron ions, use being made particularly preferably of a sodium iron-(III) gluconate complex.

The claimed contrast medium can contain as optional constituents in the liquid vehicle a sugar alcohol, such as sorbitol, maltitol, galactitol, xylitol etc., in an amount of 0 to 20% based on constituent A.

Furthermore, it is advantageous to add to the liquid vehicle as further constituent (E) a phospholipid, such as lecithin, which acts as surface-active agent and stabilizes the microscopic gas bubbles in the aqueous liquid vehicle by improving the suspension of the vegetable oil.

The liquid vehicle in the contrast medium according to the invention can contain as further constituent (F) glycerol, or as constituent (G) a preservative such as benzyl alcohol or the like.

The contrast medium according to the invention contains an electrolyte in physiological concentration, for example 0.9% sodium chloride, even though it is possible to use as aqueous liquid vehicle a Ringer solution or a Tyrode solution or even an aqueous solution of maltose, dextrose, lactose or galactose.

The aqueous liquid vehicle having a physiological electrolyte content for the contrast medium according to the invention preferably contains 1 to 5% by weight, more preferably 2 to 4% by weight, and in particular 3 to 4% by weight, of constituent A, that is to say of the pharmacologically acceptable polypeptide and/or polysaccharide and/or derivative thereof, 1 to 10% by weight, more preferably 5 to 8% by weight, and in particular 6 to 7.5% by weight, or constituent B, that is to say of the pharmacologically acceptable vegetable oil, and 0.01 to 0.05% by weight, preferably 0.02 to 0.04% by weight, of constituent C, that is to say of the pharmacologically acceptable soluble iron(III) salt.

The liquid vehicle for the claimed contrast medium can contain as further, optional, constituents 0 to 1% by weight of constituent D, that is to say of the sugar alcohol, 0 to 5% by weight, more preferably 0.01 to 2% by weight, and even more preferably 0.3 to 0.5% by weight, of constituent E, that is to say of the phospholipid, such as lecithin and 0 to 2% by weight, more preferably 0.6 to 0.9% by weight, of constituent F, that is to say glycerol.

There is dispersed in the contrast medium according to the invention a gas, such as air, nitrogen or an inert gas, helium or mixtures thereof, in an amount of 1 to 10% by volume, and even more preferably in an amount of 3 to 6% by volume, specifically in the form of bubbles with a diameter of less than 7 μm (this particle size having been measured after manual suspension of the gas bubbles in the aqueous liquid vehicle). This manual suspension comprises spraying the liquid backwards and forwards in the gas atmosphere 25 times via a three-way tap. Of course, it is also possible to disperse the gas in the aqueous liquid vehicle by the action of ultrasound, or to use for this purpose a pump driven by, for example, electricity.

The mixing of the gas into the aqueous liquid vehicle results in a homogeneous suspension which is stable for about 5 to 10 minutes, there being a phase separation after having been left to stand for only 2 minutes, the constituents A and B settling into different layers. This phase separation has no significance because the microscopic bubbles are homogeneously dispersed in the two phases. On being left to stand, as time passes the bubbles line up together to form a chain as a consequence of the surface tension on the bubbles and owing to cohesive forces. The gas bubbles are still able to pass through the capillaries even in this stage. On being left to stand for longer, several small bubbles coalesce to form larger bubbles, which occurs first at the interfaces, for example on the walls of the vessels.

The addition of constituents B and C to the liquid vehicle for the contrast medium according to the invention achieves this stabilization of the gas bubble suspension. Although it is also possible to suspend the gas bubbles in constituent A alone, the suspension thus obtained is very unstable and results in larger air bubbles after having left to stand for only 1 to 2 minutes, and these have combined to form a single air bubble after 10 minutes.

The invention furthermore relates to a process for the preparation of the contrast medium which is described above, which comprises suspension in the liquid vehicle of a gas, such as, preferably, air, manually, mechanically, for example using a pump which is driven by electricity, or by the action of ultrasound.

It is possible to use as constituent A in the preparation of the contrast medium according to the invention commercially available products which contain oxypolygelatin (Gelifundol ®), degraded gelatin (Gelafundin ® or Physiogel ®), gelatin polysuccinate (Thomaegelin ® 4% in ringer acetate), crosslinked polypeptides (Haemaccel ® 35) and dextran (dextran solution 40 ® salvia with 20% Sorbitol ®, infusion solution 10% dextran 40 ®, 20% Sorbitol ®, Longasteril 40 ® with 20% Sorbitol ®, Onkovertin N ® with Sorbitol ®, Rheofusin S 20 ®, Rheomacrodex ® with 10% Sorbitol ® 20%, dextran solution 40 ® electrolyte-free, dextran solution 40 ® salvia with 0.9% Nacl, infusion solution 10% dextran 40 ®, 0.9% NaCl, Longasteril 40 ® sodium chloride-free, Onkovertin N ®, Onkovertin N ® sodium chloride-free, Parenteral D 40 ®, Plasmafusin 40 E ®, Rheofusin ®, Rheofusin E ®, Rheofusin ® sodium chloride-free, Rheomacrodex ® 10%, Rheomacrodex ® 10% sodium chloride-free G, Rheomacrodex ® 10% sodium chloride-free S, Thomaedex 40 ® sodium chloride-free with 5% Sorbitol ® Thomaedex 40 ® with NaCl, dextran solution 60 ®, dextran solution 75 ® salvia with 0.9% NaCl, infusion solution 6% dextran 70 ® 0.9% sodium chloride, Longasteril 70 ® with electrolytes, Macrodex 4.5% RL ®, Macrodex 6% ®, Onkovertin 6% ®, Plasmafusin 60 ®, or Thomaedex 60 ® with NaCl).

It is likewise possible to use a commercial product as constituent B, namely Intralipid ®, 20% vitrum, Intralipid ®, 10% vitrum, Lipofundin ® MCT 10%, Lipofundin ® S 10% or 20%, Nutrifundin ® and Tutolipid ®.

Commercial products can also be used as constituent C, such as Ferrlecit ®, Ferreophor ®, Ferrum Hausmann ® of Jectofer ®.

On use of the contrast medium according to the invention, the latter is, after suspension of the gas in the liquid vehicle, injected intravenously, whereupon 10 ml of physiological (0.9% strength) sodium chloride solution is then injected in order, in the first place, to obtain a bolus injection and, in the second place, to prevent the subsequent uncontrolled flooding of the contrast medium out of the filled veins. It is possible in this way to obtain controlled conditions which, for example, also permit video-sensitometric evaluation of, for example, the right ventricle.

By reason of the fact that the contrast medium according to the invention produces a very stable dispersion of small microscopic bubbles with a particle size below the particle size of the red blood corpuscles, it is possible for the contrast medium to pass through the pulmonary capillaries and other very narrow vessels, and the consequence of this is that the contrast medium can be injected via the brachial vein and is transported via the pulmonary capillaries into the left atrium, the left ventricle and the ascending aorta in sufficient amount for it to be detectable there. Since the microscopic bubbles float in the blood, it is possible to visualize the blood flow, by which means it is possible to detect virtually non-invasively pathological states in the right and in the left half of the heart. Furthermore, the fine gas bubbles in the contrast medium according to the invention allow not only examination of the heart by echocardiography but also examination of other organs, such as the liver, by ultrasonic echoes. The customary contrast media are unsuitable for this, by reason of their physiological constituents and their bubble size, because flow through the narrow vessels of these organs is no longer possible.

The consequence of the short perfusion time of the contrast medium according to the invention, which is of the same order of magnitude as that of blood, is that the flow behaviour of the blood is unimpaired by the contrast medium, which opens up possibilities of considerably more accurate and improved diagnosis.

The examples which follow serve to illustrate the invention further.

EXAMPLE 1

A contrast medium is prepared from the following constituents A1, B1, C1 and air in the ratios of amounts indicated below, the constituents A1, B1 and C1 containing the constituents A, B and C according to the invention and having the following composition:

Constituent A1 (Gelifundol ®):
55.0 g oxypolygelatin
5.84 g sodium chloride
2.52 g sodium bicarbonate
0.19 g ethylenediaminetetraacetic acid (disodium salt)
0.07 g calcium chloride
ad 1000 ml water for injections Constituent B1 (Intralipid ® 20% vitrum):
200 g fractionated soya oil
12 g egg yolk lecithin
22.5 g glycerol
ad 1000 ml water for injections Constituent C1 (Ferrlecit ®):
62.5 mg iron (as sodium iron(III) gluconate complex)
45 mg benzyl alcohol (preservative)
ad 5 ml water for injections Using the above constituents A1, B1, C1 and air, the following doses of the contrast medium according to the invention are prepared:

Dose 1:
5 ml constituent A1
3 ml constituent B1
0.2 ml constituent C1
0.5 ml air
=8.7 ml Dose 2:
10 ml constituent A1
6 ml constituent B1
0.4 ml constituent C1
1 ml air
=17.4 ml Dose 3:
18 ml constituent A1
8 ml constituent B1
0.5 ml constituent C1
1.5 ml air
=28 ml The doses indicated above were divided between two injection syringes and rapidly sprayed backwards and forwards at least 25 times via a three-way tap, this resulting in a mixture which contains no visible air bubbles whatever.

The osmolality of these mixtures is 345 mosmol/kg.

Information about the resulting mixtures was first gained by examination under the light microscope, this showing that more than 99% of the resulting air bubbles have a particle size less than 5 $\mu$m.

Because of the possibility of deformation of the small air bubbles by the cover glass and the adhesive forces between the slide solution and cover glass solution, the size determination was repeated using a laser apparatus, the size determination being carried out on the microscopic bubbles both in a stationary cell and in an agitated system. This entailed the solution being suspended on one occasion manually in the agitated system, and with ultrasound in the other case. The results obtained from this are compiled in Table I below:

TABLE I

| Stationary cell Manual suspension | | Agitated system Manual suspension | | Agitated system Suspended with ultrasound | |
|---|---|---|---|---|---|
| smaller than ($\mu$m) | % of bubbles | smaller than ($\mu$m) | % of bubbles | smaller than ($\mu$m) | % of bubbles |
| 6.4 | 100 | 3.9 | 100 | 5.0 | 100 |
| 5.0 | 99.7 | 3.0 | 99.8 | 3.9 | 99.9 |
| 3.9 | 95.0 | 2.4 | 98.2 | 3.0 | 96.9 |
| 3.0 | 62.3 | 1.0 | 91.8 | 2.4 | 88.4 |
| 2.4 | 24.6 | 1.5 | 77.5 | 1.9 | 77.1 |
| 1.9 | 14.1 | 1.2 | 66.7 | 1.5 | 59.6 |
| 1.5 | 11.0 | | | 1.2 | 42.1 |
| 1.2 | 10.4 | | | | |

As is evident from Table I above, a suspension with gas bubbles having a particle size below the particle size of the red blood corpuscles is obtained, this homogeneous suspension being stable for 5 to 10 minutes, and the phase separation which then occurs being no problem because the microscopic bubbles are homogeneously dispersed in the two phases.

EXAMPLE 2

The contrast medium according to the invention was administered intravenously, in the above doses 1 to 3, via the right or left cubital vein to 27 patients from 17 to 65 years of age ($\bar{x}=39\pm19$), in order to be able to draw diagnostic conclusions about the tricuspid, mitral and aortic valves and about left-ventricular flow behaviour. The sole prerequisite for the echocardiographic examination was that the patients were suitable for sonography. At the start, dose 1 was always used. Since the injections were tolerated by all the patients without the slightest side effects, where the diagnostic aim was appropriate the dose was raised to correspond to doses 2 and 3. Table II below give an overview of the spectrum of the disorders of the patients who were examined.

TABLE II

| No. | Pat. | Age (years) | Diagnoses | ECG changes during injection |
|---|---|---|---|---|
| 1 | H.P. | 57 | Post anterior wall infarct | none |
| 2 | T.B. | 18 | Thrombus r.atrium | = |
| 3 | G.H. | 25 | Thrombus l.ventricle | = |
| 4 | F.M. | 20 | AVR (Bjork Shiley V.) | = |
| 5 | N.G. | 29 | TI grade II | = |
| 6 | A.D. | 73 | AS grade IV | = |
| 7 | S.K. | 31 | AS grade II, AI grade III | = |
| 8 | R.R. | 57 | CC stage III | = |
| 9 | M.E. | 45 | Rhythm disturbances | = |
| 10 | A.S. | 60 | Pulmonary emphysema | = |
| 11 | V.R. | 49 | MVR (Wada-Cutter V.) | = |
| 12 | J.A. | 17 | Bicuspid aortic valve | = |
| 13 | H.H. | 47 | Post pulmonary embolisms, TI | = |
| 14 | N.B. | 51 | AI grade II | = |
| 15 | K.K. | 18 | Mitral valve prolapse | = |
| 16 | A.W. | 19 | PS grade I, PI grade I | = |
| 17 | F.G. | 59 | Defective orifice pulmonary v. | = |
| 18 | C.E. | 60 | MVR (Bjork Shiley V.) | = |
| 19 | S.W. | 19 | TI grade II - III | = |
| 20 | F.F. | 16 | AS grade I - II, susp. MI | = |
| 21 | H.W. | 48 | AI grade IV | = |
| 22 | H.F. | 55 | AI grade IV | = |
| 23 | A.V. | 45 | Left bundle-branch block | = |
| 24 | M.D. | 49 | CC stage II - III | = |
| 25 | S.L. | 26 | Pulmonary hypertension | = |
| 26 | G.H. | 20 | IHSS | = |
| 27 | F.H. | 65 | MVR (Bjork Shiley V.) | = |

Abbreviations: AVR = aortic valve replacement, V. = valve, TI = tricuspid insufficiency, AS = aortic stenosis, AI = aortic insufficiency, CC = congestive cardiomyopathy, MVR = mitral valve replacement, PS = pulmonary stenosis, PI = pulmonary insufficiency, IHSS = idiopathic hypertrophic subaortic stenosis With this injection of the contrast medium according to the invention, at all the doses used there was no significant change either in the heart rate or in the systolic or diastolic blood pressure, reference being made to Table III below in this connection.

TABLE III

| | Heart rate | | | BP syst. | | | BP diast. | | |
|---|---|---|---|---|---|---|---|---|---|
| | before | after | S | before | after | S | before | after | S |
| Dose 1 | 75 ± 18 | 73 ± 18 | p > 0.05 | 121 ± 13 | 121 ± 14 | p > 0.05 | 77 ± 17 | 77 ± 17 | p > 0.05 |
| Dose 2 | 71 ± 14 | 71 ± 13 | p > 0.05 | 121 ± 14 | 124 ± 13 | p > 0.05 | 77 ± 17 | 77 ± 17 | p > 0.05 |
| Dose 3 | 71 ± 19 | 72 ± 18 | p > 0.05 | 121 ± 10 | 127 ± 16 | p > 0.05 | 72 ± 22 | 73 ± 23 | p > 0.05 |

As the amount of intravenously administered contrast medium increased, detection of the contrast medium in the left ventricle took place increasingly early, but the limit of significance comparing dose 1 with dose 2 and dose 3 was not reached. In addition, as the dose was raised the contrast medium was detectable in the left ventricle for longer times, significant changes being detectable, reference being made to Table IV below in this context.

TABLE IV

| | Duration of detection of bubbles in the l.v.(s) | Number of systoles to detection in the l.v. |
|---|---|---|
| Dose 1 | (n = 23) 22 ± 15 | 4.5 ± 3.4 |
| Dose 2 | (n = 19) 39 ± 34* | 3.6 ± 2 |
| Dose 3 | (n = 5) 75 ± 40** | 2.8 ± 2.1 |

In total, disturbances of left-ventricular function were detected in nine patients. Aortic insufficiency was diagnosed for four patients (Patient Nos. 2, 4, 21 and 22), this being confirmed by angiocardiography. In one female patient (No. 18) regurgitation over a Bjork-Shiley prosthesis in the mitral position was detected unambiguously, the Doppler echocardiogram being unable to detect regurgitation in this patient. For one patient it was possible to rule out a leak in a Bjork-Shiley valve, this agreeing with the Doppler echocardiogram. Furthermore, clinically suspected mitral insufficiency in three patients could be ruled out (Nos. 7, 20 and 24). In addition, myocardial staining was seen for one patient (No. 12).

Thus, the conclusion is that it is possible with the aid of peripheral venous injection of the contrast medium according to the invention to pass via the right atrium and the right ventricle through the pulmonary capillaries and thus to reach the left ventricle and the ascending aorta with the contrast medium.

No side effects whatever occurred in any of the patients examined, nor were any subjective or objective manifestations observed after passage into the left ventricle and subsequently into the cerebral vascular system. Nor did any side effects occur in two patients known to be allergic to iodine (cardiac catheter examination of one patient had to be terminated) and one patient allergic to plasters. The heart rate did not change before and after the injection. Likewise, there was no statistically significant change in the blood pressure. There was an increase in the systolic blood pressure of 3 mmHg with dose 2 and of 6 mmHg with dose 3 (p>0.05).

As the dose increases the microscopic bubbles are detected increasingly early in the left ventricle (Table IV), the numbers of patients available being insufficient to allow statistical confirmation of the differences. A mean of 4.5 right-ventricular systoles are needed with dose 1, and 2.8 right-ventricular systoles are needed with dose 3. This indicates that the appearance time depends on the number of microscopic bubbles and on the echocardiographic detectability, that is to say on the system which is to be resolved. However, the number of 2.8 systoles also indicates that the detectability is already almost within the range of physiological passability through the pulmonary capillaries. The duration of detection in the left ventricle is also dose-dependent (Table IV), that is to say the duration of detection likewise depends on the number of microscopic bubbles injected. In addition, the long detectability of the microscopic bubbles with dose 3 (75+40 s) indicates high stability of the microscopic bubbles and thus of the claimed contrast medium.

With the aid of the contrast medium according to the invention, which passes through the pulmonary capillaries, it is possible to extend contrast medium echocardiography outside the range of indications for it prevailing hitherto, and to make it possible to assess noninvasively flow at the left-ventricular valves and in the left ventricle. Going beyond Doppler echocardiography, it is possible to detect the flow in many planes, to assess even artificial valves in the left ventricle, and to produce a visual dynamic demonstration of the blood flow in all structures of the left ventricle. Thus, inter alia, it is even possible to observe the impact of the microscopic bubbles on the valve framework or on the valve lid. Furthermore, the contrast medium according to the invention makes it possible to assess intrapulmonary right-left shunts and the passage times in the pulmonary capillaries.

We claim:

1. Contrast medium using a suspension of gas bubbles for ultrasonic examinations in a physiologically acceptable aqueous liquid vehicle having a physiological electrolyte content, comprising: a liquid vehicle containing in admixture by weight:
   (A) 1 to 5 percent of a polysaccharide gelatin or a gelatin derivative including oxypoly gelatin, degraded gelatin, gelatin polysuccinate, cross linked polypeptide, dextran or a mixture thereof,
   (B) 1 to 10 percent of a pharmacologically acceptable vegetable oil selected from the group consisting of soja oil, maise oil, sesame oil, arachis oil, or mixtures thereof and
   (C) 0.01 to 0.05 percent of a pharmacologically acceptable soluble iron (III) salt; and
   wherein the gas comprises air, nitrogen or inert gas or mixtures thereof in bubbles smaller in diameter than 7 $\mu$m.

2. Contrast medium according to claim 1, characterized in that the liquid vehicle contains as further constituent
   (D) 0 to 20% (based on constituent A) of a sugar alcohol.

3. Contrast medium according to claim 1, characterized in that the liquid vehicle contains as further constituent
   (E) a phospholipid.

4. Contrast medium according to claim 1, characterized in that the liquid vehicle contains as further constituent
   (F) glycerol.

5. Contrast medium according to claim 1, characterized in that the liquid vehicle contains as further constituent
   (G) a preservative.

6. Contrast medium according to claim 1, characterized in that the liquid vehicle contains as pharmacologically acceptable soluble iron (III) salt a Sodium iron-(III) gluconate complex.

7. Contrast medium according to claim 1 wherein the liquid vehicle contains as sugar alcohol at least one member selected from the group consisting of sorbitol, maltito, galactitol xylitol.

8. Contrast medium according to claim 1, characterized in that the liquid vehicle contains as phospholipid lecithin.

9. Contrast medium according to claim 4, characterized in that the liquid vehicle contains
   1 to 5% by weight of constituent (A),
   1 to 10% by weight of constituent (B),
   0.01 to 0.05% by weight of constituent (C),
   0 to 1% by weight of constituent (D),
   0 to 5% by weight of constituent (E),
   0 to 2% by weight of constituent (F) and
   1 to 10% by volume of a gas in the form of bubbles with a diameter of less than 7 $\mu$m.

10. Process for the preparation of the contrast medium according to claim 1, suspending said gas in said liquid vehicle manually, mechanically or by the action of ultrasound to form bubbles thereof having diameters less than 7 nm.

* * * * *

UNITED STATES PATENT AND TRADEMARK OFFICE
CERTIFICATE OF CORRECTION

PATENT NO. : 4,832,941

DATED : May 23, 1989

INVENTOR(S) : BERWING, et al.

It is certified that error appears in the above-identified patent and that said Letters Patent is hereby corrected as shown below:

Column 9, line 13 (claim 1, line 6), "polysaccharide gelatin" should read --polysaccharide, gelatin--.

Signed and Sealed this

Thirteenth Day of August, 1991

Attest:

HARRY F. MANBECK, JR.

Attesting Officer

Commissioner of Patents and Trademarks